(12) United States Patent
Lima et al.

(10) Patent No.: US 11,299,825 B2
(45) Date of Patent: Apr. 12, 2022

(54) MANUFACTURING OF ARTIFICIAL MUSCLE ACTUATORS

(71) Applicant: Lintec of America, Inc., Richardson, TX (US)

(72) Inventors: Marcio Dias Lima, Richardson, TX (US); Sergey Li, Richardson, TX (US)

(73) Assignee: LINTEC OF AMERICA, Richardson, TX (US)

( * ) Notice: Subject to any disclaimer, the term of this patent is extended or adjusted under 35 U.S.C. 154(b) by 218 days.

(21) Appl. No.: 16/488,970

(22) PCT Filed: Feb. 27, 2018

(86) PCT No.: PCT/US2018/019929
§ 371 (c)(1),
(2) Date: Aug. 27, 2019

(87) PCT Pub. No.: WO2018/160555
PCT Pub. Date: Sep. 7, 2018

(65) Prior Publication Data
US 2020/0000572 A1    Jan. 2, 2020

Related U.S. Application Data

(60) Provisional application No. 62/465,003, filed on Feb. 28, 2017.

(51) Int. Cl.
*D02J 13/00* (2006.01)
*A61F 2/08* (2006.01)
(Continued)

(52) U.S. Cl.
CPC .............. *D02J 13/001* (2013.01); *A61F 2/08* (2013.01); *D01F 8/12* (2013.01); *D01F 8/18* (2013.01);
(Continued)

(58) Field of Classification Search
CPC .......... D02G 1/004; D02G 1/02; D01H 13/28; D02J 13/001
See application file for complete search history.

(56) References Cited

U.S. PATENT DOCUMENTS 3,488,934 A * 1/1970 MacDonald ............. A46D 1/00
57/282
4,086,751 A   5/1978 Hino et al.
(Continued)

FOREIGN PATENT DOCUMENTS

CN      105696138 A    6/2016
JP      2010-65339     3/2010
(Continued)

OTHER PUBLICATIONS

Taiwanese Official Letter and Search Report issued in corresponding Taiwanese Patent Application No. 107106856 dated Feb. 4, 2020 (13 pages).
(Continued)

*Primary Examiner* — Shaun R Hurley
(74) *Attorney, Agent, or Firm* — Greenblum & Bernstein, P.L.C.

(57) ABSTRACT

Methods and a device for the continuous manufacturing of artificial muscle actuator device fibers are disclosed. The method includes: threading an untwisted fiber along the axis of a tube and inside the tube that includes a heating means to raise the localized temperature of a cross-section of the tube to a predetermined temperature; providing a tension on the untwisted fiber; and twisting the untwisted fiber while the fiber is within the tube.

13 Claims, 5 Drawing Sheets

(51) Int. Cl.
*D01F 8/12* (2006.01)
*D01F 8/18* (2006.01)
*D02J 1/18* (2006.01)
*F03G 7/06* (2006.01)
*D02G 1/02* (2006.01)

(52) U.S. Cl.
CPC ............... *D02J 1/18* (2013.01); *F03G 7/06* (2013.01); *D02G 1/02* (2013.01)

(56) References Cited

U.S. PATENT DOCUMENTS

| | | | |
|---|---|---|---|
| 4,322,944 A | 4/1982 | Sraitr et al. | |
| 4,888,945 A * | 12/1989 | Maeda | D01H 13/005 57/264 |
| 5,390,400 A * | 2/1995 | Jacob | F28C 3/005 28/274 |
| 6,449,938 B1 * | 9/2002 | Kutsenko | D01H 1/115 57/350 |
| 8,116,899 B1 | 2/2012 | Johnson et al. | |
| 9,708,736 B2 * | 7/2017 | Agarwal | D02G 3/328 |
| 9,784,249 B2 * | 10/2017 | Li | D02G 3/448 |
| 10,154,895 B2 * | 12/2018 | Hiraoka | A61F 7/00 |
| 2002/0079610 A1 | 6/2002 | Uy et al. | |
| 2003/0167748 A1 * | 9/2003 | Wortmann | D02G 1/20 57/284 |
| 2015/0152852 A1 * | 6/2015 | Li | D01F 6/00 60/528 |
| 2015/0219078 A1 * | 8/2015 | Li | H02N 10/00 310/306 |
| 2017/0035550 A1 * | 2/2017 | Hiraoka | A61F 7/00 |
| 2017/0314539 A1 | 11/2017 | Kim et al. | |
| 2017/0369318 A1 * | 12/2017 | Inoue | D07B 1/005 |
| 2018/0291535 A1 | 10/2018 | Ridley et al. | |
| 2020/0115827 A1 * | 4/2020 | Kawahara | D02G 1/02 |

FOREIGN PATENT DOCUMENTS

| | | |
|---|---|---|
| WO | 200138620 A1 | 5/2001 |
| WO | 2016064220 A1 | 4/2016 |
| WO | 2018/020795 A1 | 2/2018 |
| WO | 2018/020796 A1 | 2/2018 |
| WO | 2018/106926 A1 | 6/2018 |
| WO | 2018/156761 A1 | 8/2018 |

OTHER PUBLICATIONS

International Preliminary Report on Patentability and Written Opinion issued in corresponding International Application No. PCT/US2018/019929 dated Sep. 12, 2019 (7 pages).
Japan Official Action received in JP Application No. 2019-546886, dated Oct. 5, 2020 and English language translation thereof.
Notice of Reasons for Rejection received in JP Application No. 2019-546886, dated Jul. 5, 2021 and English language translation thereof.
International Preliminary Report on Patentability including Written Opinion issued in PCT/US2018/019929, dated Sep. 3, 2019.
International Search Report issued in PCT/US2018/019929, dated Apr. 16, 2018.

\* cited by examiner

MANUFACTURING OF ARTIFICIAL MUSCLE ACTUATORS

FIELD OF INVENTION

The present invention relates to the structure, fabrication, and operation of thermal and chemical artificial muscle actuators.

CROSS REFERENCE TO RELATED APPLICATIONS

The material of the following applications may be used in conjunction with embodiments disclosed herein: U.S. Provisional Application No. 62/465,003, entitled "MANUFACTURING OF ARTIFICIAL MUSCLE ACTUATORS," filed on Feb. 28, 2017; U.S. Provisional Application No. 62/590,121, entitled "EMBEDDED CONDUCTIVE WIRES IN POLYMER ARTIFICIAL MUSCLE ACTUATING DEVICES," filed on Nov. 22, 2017; WIPO Application No. PCT/US2017/030199, filed on Apr. 28, 2017; as well as U.S. Provisional Application No. 62/577,512, filed on Oct. 26, 2017 and entitled "SHEET WRAPPING MUSCLES." These applications are hereby incorporated by reference in their entirety.

BACKGROUND OF INVENTION

Thermally driven torsional actuators based on twisted polymeric and carbon nanotube (CNT) fibers and yarns have a wide range of applications. Artificial muscle actuators comprising twisted and/or coiled polymers have the advantage of low cost, high production volume, and design simplicity. Artificial muscle actuators may have advantages over small motors because of the greatly simplified engineering and lower product costs.

SUMMARY OF INVENTION

In one aspect, embodiments of the invention relate to a method for the continuous manufacturing of artificial muscle actuator device fibers. The method includes threading an untwisted fiber along the axis of a tube and inside the tube. The tube includes a heating means to raise a localized temperature of a cross-section of the tube to a predetermined temperature. Tension is provided on the untwisted fiber, and the method includes twisting the untwisted fiber while the fiber is within the tube.

In another aspect, embodiments of the invention relate to a device for the continuous manufacturing of artificial muscle actuator device fibers. The device includes at least one tube, and one or more heating means disposed on the at least one tube for locally heating a cross sectional area of the at least one tube. The heating means raises a localized temperature of a cross-section of the at least one tube to a predetermined temperature.

Other aspects and advantages of the invention will be apparent from the following description and the appended claims.

BRIEF DESCRIPTION OF DRAWINGS

Certain embodiments of the disclosure will hereafter be described with reference to the accompanying drawings, where like reference numerals denote like elements. It should be understood, however, that the accompanying figures illustrate the various implementations described herein and are not meant to limit the scope of various technologies described herein.

DETAILED DESCRIPTION

Figure 1:
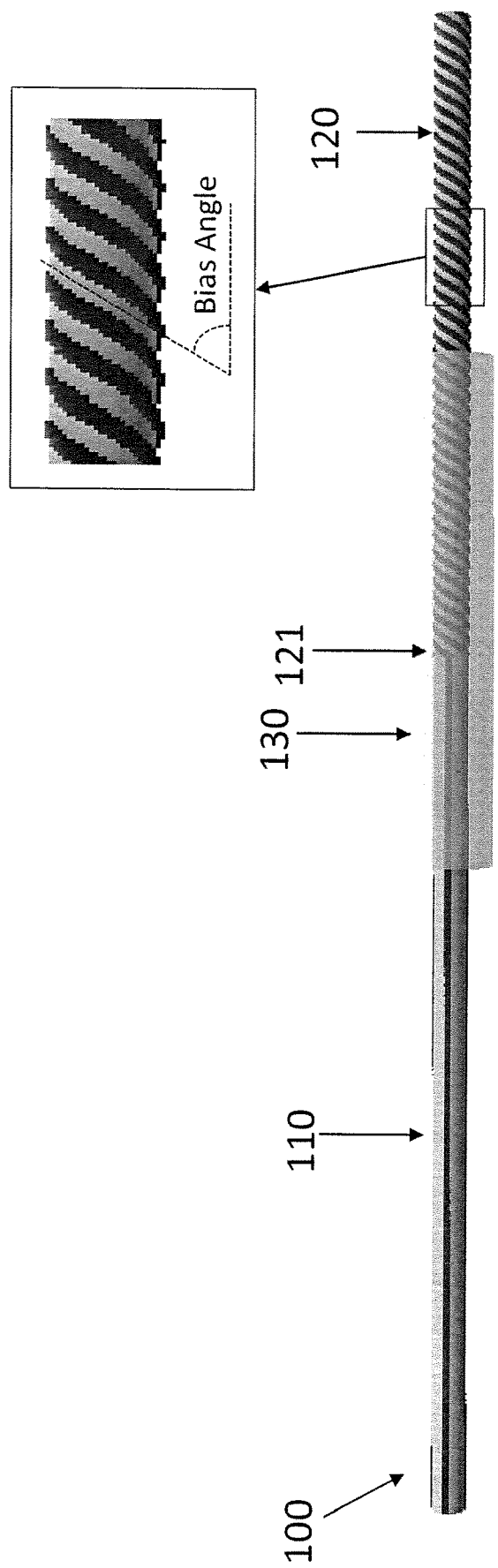
FIG. 1 shows a diagram in accordance with one or more embodiments of the invention.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to a device for manufacturing and a method for manufacturing actuator materials, or artificial muscles. Embodiments of the actuator fiber materials include twist-spun fibers that generate torsional and/or tensile actuation when are heated electrically, photonically, thermally, chemically, by absorption, or by other means. Embodiments of the invention include the manufacturing of actuators fiber materials that utilize twisted or coiled artificial muscle fibers and may be either neat or include a guest material.

Conventionally, production of twisted artificial muscle fibers (herein after, twisted fibers) is considered a batch-to-batch process, resulting in a few meters of twisted fibers in each batch. Efficient and reliable continuous manufacturing of large quantities of twisted fibers may facilitate the widespread commercial use of artificial muscles and lower the cost of manufacturing of the artificial muscles.

Upon applying a rotational force to an artificial muscle fiber in a continuous twisting and spinning apparatus, the artificial muscle fiber may twist at many different locations along its length. This may lead to too much twist accumulating at a specific location along the length and the fiber. In addition, too much twist accumulating at a specific location may produce snarls, i.e., the artificial muscle fiber twists upon itself resulting in a "twisted-kink" along the axis of the fiber. Such snarls prevent applying a proper and/or uniform twist to the artificial muscle fiber, and therefore, must be removed before manufacturing can resume.

Embodiments disclosed herein include an apparatus for continuously manufacturing and a method of continuously manufacturing twisted fibers and coiled artificial muscle fibers (hereinafter, coiled fibers), where the coiled fibers may be twisted fibers or untwisted artificial muscle fibers (hereinafter, untwisted fiber).

There is a relationship between tension, twisting and snarling. For example, the greater the tension on the artificial muscle fiber, the greater twist may be applied without allowing the artificial muscle fiber to snarl. However, when the tension exceeds the strength of the artificial muscle fiber, the artificial muscle fiber may break. Because the amount of applied tension is limited by tensional strength of the artificial muscle fiber, the amount of twist that may be inserted into the fiber is limited to the occurrence of the snarl along the artificial muscle fiber at the tensional strength of the artificial muscle fiber. One of ordinary skill in the art will appreciate that the above considerations are also a function of the size and material of the artificial muscle fiber.

According to one or more embodiments, the higher the bias angle of the muscle fiber, the more torque the artificial muscle fiber actuator may produce during operation. In this context, the bias angle refers to the relative angle between the fiber and a central axis of the twisted fiber. In embodiments disclosed herein, the bias angle is directly related to the specific actuation properties, and may be varied accordingly.

In accordance with embodiments disclosed herein, to achieve the largest possible bias angle, it may be necessary to twist the artificial muscle fiber to the greatest extent possible; however, there is a maximum amount of twist that may be inserted in the artificial muscle fiber before the fiber snarls, or breaks under excessive tension. One or more embodiments disclosed herein provide an apparatus or a method to insert twist and prevent snarling at loads are low enough to prevent the artificial muscle fiber from breaking. One or more embodiments of the invention also provide an apparatus or a method for continuously twisting a fiber inside a tube in order to produce a coiled muscle fiber, i.e., in the shape of a coil, without snarling the fiber. According to one or more embodiments, the resulted coiled muscle fiber may be twisted or untwisted.

FIG. 1 illustrates an apparatus for twisting an artificial muscle fiber in accordance with one or more embodiments of the invention. The artificial muscle fiber 100 passes through a first tube 130 that may include one or more heating sections that increase the temperature of the artificial muscle fiber 100 locally or in an area at a specific location making that specific location of the fiber softer and more malleable. Upon application of a rotational force to the artificial muscle fiber 100 in order to twist the artificial muscle fiber 100, the artificial muscle fiber 100 twists in that specific location, which applies the least amount of internal torsional resistance. Thus, softening the artificial muscle fiber 100 in that specific location (hereinafter, twisting point 121). The localized heating as the specific location insures that the twist will occur at the twisting point 121 of the artificial muscle fiber 100. One of ordinary skill in the art will appreciate that such an apparatus may include multiple heating sections and the heating section/sections may increase (or decrease) the temperature at multiple locations of the artificial muscle fiber 100. One of ordinary skill in the art would also appreciate that the apparatus may be designed in order that the twisting point 121 may be a localized single point, multiple localized points, an area, or multiple areas along the length of the fiber, depending on the desired application.

According to one or more embodiments, the first tube 130 may be a metallic tube or may include a metallic tube. In order to increase the temperature of a section of the metallic tube, the section may be heated via resistive heating. According to one or more embodiments, a heating means may provide an electrical current to the heating section of the first tube 130. According to one or more embodiments, a thermocouple may control the temperature of the heating section. The thermocouple may be disposed on the heating section of the first tube 130.

According to one or more embodiments, the heating section locally heats up a cross-sectional point on the artificial muscle fiber 100. According to one or more embodiments, the heating section heats up an area of the artificial muscle fiber 100.

In the view of FIG. 1, the artificial muscle fiber 100 moves from left to right with respect to the first tube 130. An untwisted/uncoiled fiber 110 enters the first tube 130 as the artificial muscle fiber 100 continues twisting at the twisting point 121. The twisting point 121 may substantially overlap the heating section of the first tube 130. As the softened part of the artificial muscle fiber 100 moves away from the heating section, the softened part cools down and becomes more rigid. One or ordinary skill in the art will appreciate that sections of the tube also may be cooled by other means. Accordingly, as the artificial muscle fiber 100 moves in the first tube 130, a twisted fiber 120 exits the first tube 130.

According to one or more embodiments, the bias angle of the twisted fiber 120 may be ~45 degrees. In other embodiments, the bias angle of the twisted fiber 120 may be ~53 degrees, or may exceed ~53 degrees. The specific bias angle may be selected based on the desired final properties of the artificial muscle actuator. The values given above are directed to maximizing the available torque; however, in some applications, the maximum available torque may not be desired.

According to one or more embodiments of the invention, the first tube 130 physically constrains the soft twisted fiber in order to prevent snarling at the twisting point 121 or other parts of the fiber where the twisted fiber may still be soft. According to one or more embodiments, the inner diameter of the first tube 130 may be only slightly larger than the diameter of the artificial muscle fiber 100. In some embodiments, the diameter of the first tube 130 may be determined based on diameter of the artificial muscle fiber 100 desired.

According to one or more embodiments of the invention, the artificial muscle fiber 100 may be made of a material, the material can be, but not limited to, a polymer based fiber. For example, nylon 6, nylon 6,6, polyethylene, polyvinylidene fluoride, Nylon 6,10, Nylon 6,12, liquid crystalline polymers such as polyarylate, and any combinations thereof. According to one or more embodiments the artificial muscle fiber 100 may also include carbon nanotubes (CNT) based materials.

While twisting an artificial muscle fiber 100, if the twist exceeds a specific amount, the artificial muscle fiber 100 may coil. However, conventional methods for coiling the artificial muscle fiber 100 by only increasing the twist in the artificial muscle fiber 100 increases the risk of creating snarls along the artificial muscle fiber 100.

Figure 2:
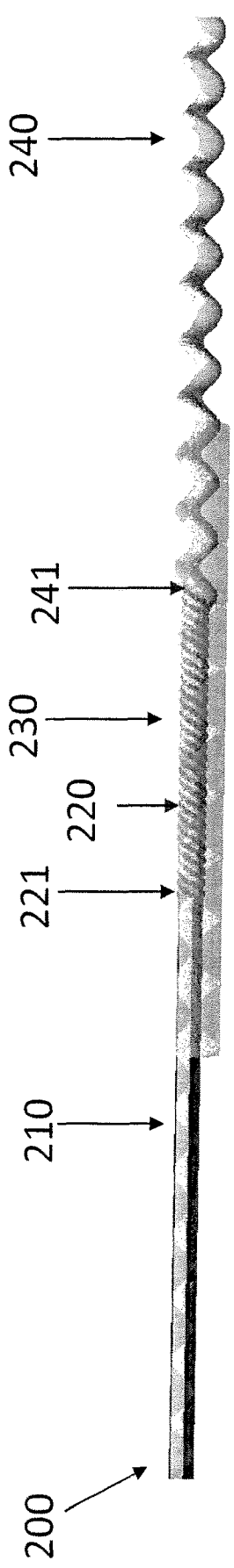
FIG. 2 shows a diagram in accordance with one or more embodiments of the invention.

FIG. 2 illustrates a device for twisting and/or coiling an artificial muscle fiber 200 without snarling in accordance with one or more embodiments of the invention. By choosing a specific diameter of the first tube 230, the artificial muscle fiber 200 can be simultaneously twisted and coiled. The inner diameter of the first tube 230 may be large enough to permit the coiling of the artificial muscle fiber 200, but small enough to prevent snarling of the artificial muscle fiber 200.

According to one or more embodiments, the artificial muscle fiber 200 may twist in one location and then coil in another location along the first tube 230.

According to one or more embodiments, as a non-limiting example, the inner diameter of the first tube 230 may be 10-20% larger than the diameter of the untwisted/uncoiled fiber 210 for coiling. Such coiling may be performed on an initially twisted fiber 120, 220 or an untwisted/uncoiled fiber 210.

According to one or more embodiments, as a non-limiting example, if nylon 6,6 is used as the fiber material, the inner diameter of the first tube 230 may be approximately twice the diameter of the untwisted/uncoiled fiber 210.

According to one or more embodiments, the first tube 230 may have one or a plurality of heating sections. In addition, the first tube 230 may have one or a plurality of sections with different inner diameters across its length. According to one or more embodiments, the temperature of a twisting point 221 may be different from the temperature of a coiling point 241. According to one or more embodiments, the inner diameter of the first tube 230 at the coiling point 241 may be different from the inner diameter of the first tube 230 at the twisting point 221. For example, the inner diameter of the first tube 230 at the coiling point 241 may be larger than the inner diameter of the first tube 230 at the twisting point 221.

According to one or more embodiments, the first tube 230 may have multiple inner diameters across the length of the tube. This may make it possible to twist and/coil the artificial muscle fiber 200 differently, as the fiber moves through the first tube 230. For example, the inner diameter of the first tube 230 at the location that the fiber twists may be different from the inner diameter of the first tube 230 at the location that the fiber coils.

In FIG. 2, the twisting and coiling processes are illustrated as distinct and separated areas in the heating tube. According to one or more embodiments, the coiling and twisting may also occur substantially at the same locations within the first tube 230.

In view of FIG. 2, the artificial muscle fiber 200 moves from left to right with respect to the first tube 230 and an untwisted/uncoiled fiber 210 enters the first tube 230 as the artificial muscle fiber 200 continues twisting and/or coiling at the twisting point 221 and/or the coiling point 241. When the softened part of the artificial muscle fiber 200 moves away from the heating sections, the softened fiber cools down and becomes more rigid. Consequently, a coiled fiber 240 that may be twisted exits the right end of the first tube 230 in view of FIG. 2.

According to one or more embodiments, the inner diameter of the first tube 230, 130 may vary between materials that are used to make the artificial muscle fiber 100, 200, because some fibers may form tighter coiled structures than other fibers. As previously described, heating may also be applied at a specific location of the first tube 230 to soften the fiber and ensure the twisting and/or coiling occurs within the tube. According to one or more embodiments, the temperature of the artificial muscle fiber 230 at the twisting point 221 or the coiling point 241 may be raised to at least the glass transition temperature for the material of the artificial muscle fiber 200 and below the melting temperature for the material of the artificial muscle fiber 200.

In one or more embodiments, a second tube may be used after the first tube 130, 230. After the twisted fiber 120 or the coiled fiber 240 exits the first tube 130, 230 they enter the second tube. The second tube anneals and relaxes the twisted fiber 120 or the coiled fiber 240 making the resultant fiber (twisted, coiled, or otherwise) retain the resultant orientations without unwinding, even if the tension were released. In one or more embodiments, the second tube may operated at a temperature of at least the same temperature as the first tube 130, 230. In one or more embodiments, the heating temperature of second tube may be slightly greater than that of the first tube 130, 230.

In one or more embodiments, the first tube 130, 230 may be used to anneal a fiber that was twisted by other means, as in a traditional batch manufacturing processes. One or more embodiments disclosed herein may utilize a single tube, which provides the functions of both the first tube 130, 230 and the second tube.

Figure 3:
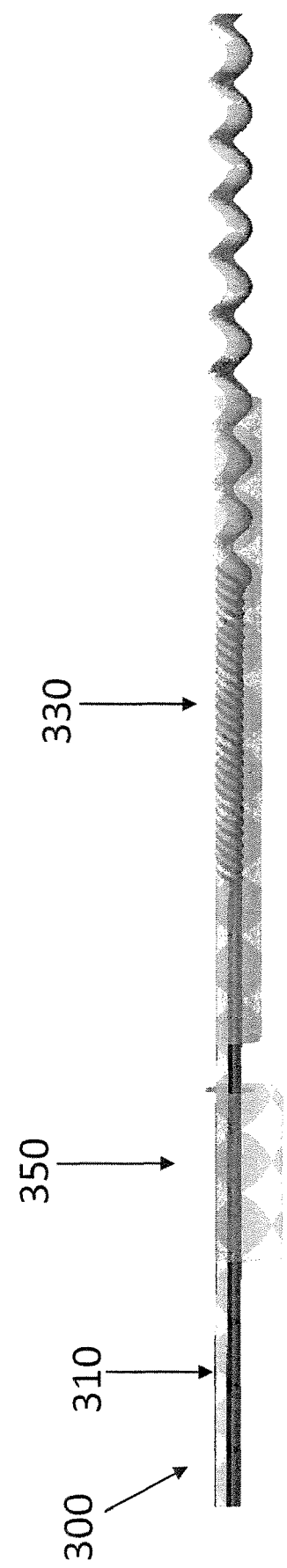
FIG. 3 shows a diagram in accordance with one or more embodiments of the invention.

FIG. 3 illustrates a device for drying the artificial muscle fiber 300 in accordance with one or more embodiments of the invention. Moisture may affect the behavior of some artificial muscle materials, for example Nylon. According to one or more embodiments, the moisture of the untwisted/uncoiled fiber 310 may be reduced to a limited amount before twisting or coiling. For example, a drying chamber 350 or moisture collection strip may be used to dry the untwisted/uncoiled fiber 310 before getting soft in the first tube 330. Such a drying section may also be incorporated into the first tube 330. For example, the first tube 330 may include moisture collection materials.

Figure 4:
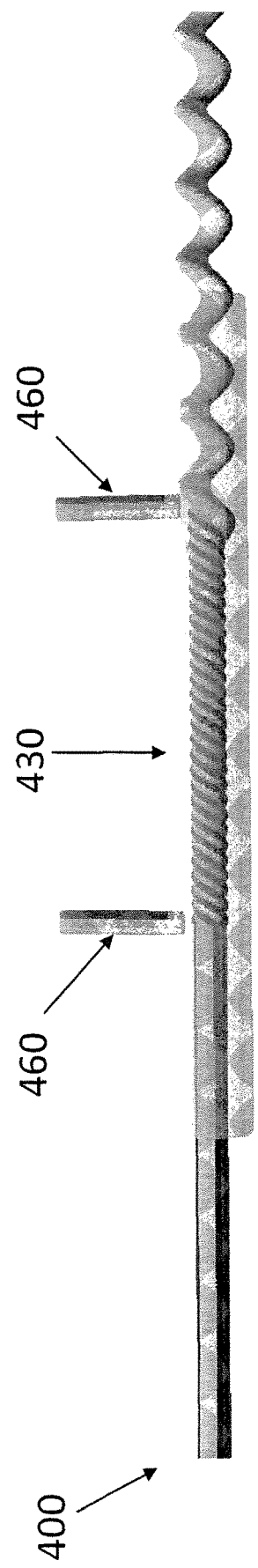
FIG. 4 shows a diagram in accordance with one or more embodiments of the invention.

FIG. 4 illustrates one or more coaters 460 that may apply a coating to the artificial muscle fiber 400 while the fiber is inside the first tube 430 in accordance with one or more embodiments. The coaters 460 may apply a coating on the artificial muscle fiber 400 at any time, i.e., before heating the fiber, after heating the fiber, or while heating the fiber. The coating may be applied at specific locations within the first tube 430 in accordance with one or more embodiments, so that the coating may be applied at any specific locations of the fiber. In one or more embodiments, the coating may be applied while the fiber is outside the tube according to known techniques. According to one or more embodiments, an inert gas may be supplied inside the first tube 430 to prevent any oxidation or chemical reactions inside the first tube 430.

According to one or more embodiments, the coating may be similar to the coating disclosed in WIPO Application No. PCT/US18/19225, entitled "CONTINUOUS PRODUCTION OF MUSCLE FIBERS," filed on Feb. 22, 2018, and WIPO Application No. PCT/US17/65127, entitled "IMPROVEMENTS IN ARTIFICIAL MUSCLE ACTUATORS," filed on Dec. 7, 2017. The contents of these applications are hereby incorporated by reference in their entirety.

In one or more embodiments, a lubricant may be supplied inside the tube to facilitate the twisting process. For these embodiments, a relatively lighter oil, such as a silicon based oil, may be used.

In one or more embodiments disclosed herein, the first tube 130, 230, 330, 430 may be composed of metal. In these embodiments, the first tube 130, 230, 330, 430 may be resistively heated. Other heating methods known in the art for heating the metal tube may be used. For example, a heating element may be directly attached to the specific location in the first tube 130, 230, 330, 430.

Figure 5:
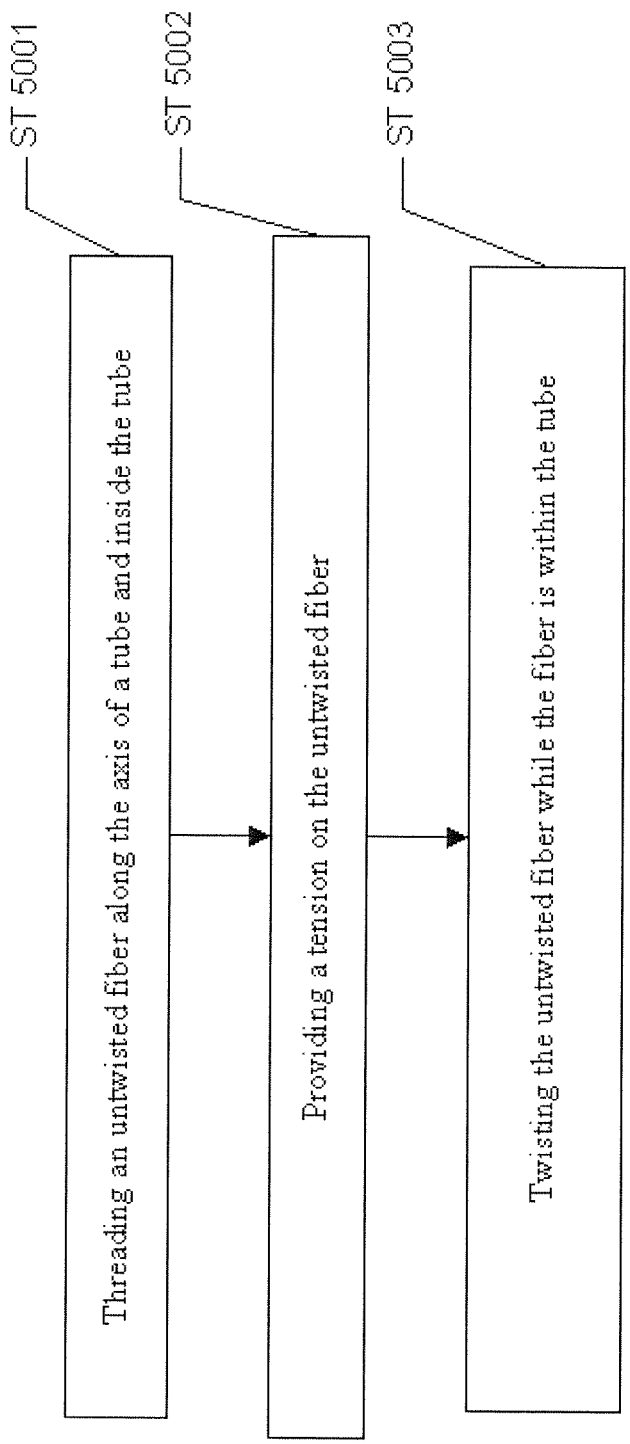
FIG. 5 shows a flow chart in accordance with one or more embodiments of the invention.

FIG. 5 illustrates a flow chart for a method for continuously manufacturing the twisted artificial muscle fiber in accordance with one or more embodiments of the invention. The methods disclosed herein may include threading an untwisted fiber along the axis of a tube and inside the tube (ST 5001), and providing a tension on the untwisted fiber (ST 5002). The method includes twisting the untwisted fiber while the fiber is within the tube (ST 5003). The aforementioned fiber and tube in one or more method may be the artificial muscle fiber 100, 200, 300, 400 and the first tube 130, 230, 330, 430 disclosed above. In one or more methods, the first tube 130 may include one or more heating sections that increase the temperature of the artificial muscle fiber 100 at a twisting point 121 to make the fiber softer and more malleable at the twisting point 121. Methods disclosed herein may include applying an appropriate tension on the artificial muscle fiber 100. Methods disclosed herein may include application of a rotational force to the artificial muscle fiber 100 that twists the artificial muscle fiber 100 in the twisting point 121, which is softened and has the least amount of internal torsional resistance.

As the artificial muscle fiber 100 passes through the first tube 130, the heated and twisted part of the artificial muscle fiber 100 moves away from the heating section of the first tube 130, cools down, and becomes more rigid. Accordingly, as the artificial muscle fiber 100 passes through the first tube 130, a twisted fiber 120 exits the first tube 130. One of ordinary skill in the art appreciates that such a method may include heating more than one section of the artificial muscle fiber 100. One of ordinary skill in the art would appreciate that in the methods described herein, the twisting point 121 may be a localized single point, multiple localized points, an area, or multiple areas along the length of the fiber.

In one or more methods described herein, the soft twisted part of the artificial muscle fiber 100 may be cooled via a cooling section.

In one or more methods described herein, the first tube 130 may be a metallic tube or may include a metallic tube. In order to increase the temperature of a location of the metallic tube, it may be heated via resistive heating.

In one or more methods described herein, the bias angle of the twisted fiber 120 may be selected as previously described.

In one or more methods described herein, the first tube 130 may physically constrain the soft twisted fiber in order to prevent snarling at the twisting point 121 or other parts of the fiber that the twisted fiber may be still soft. According to one or more embodiments, the inner diameter of the first tube 130 may be only slightly larger than the diameter of the artificial muscle fiber 100.

One or more methods disclosed herein may include coiling an artificial muscle fiber 200 without snarling. By choosing a specific diameter for the first tube 230, the artificial muscle fiber 200 can be simultaneously twisted and coiled. The inner diameter of the first tube 230 may be designed large enough to permit the coiling of the artificial muscle fiber 200, but small enough to prevent snarling of the artificial muscle fiber 200.

As noted above, in one or more methods described herein, the artificial muscle fiber 200 may twist in one location and then coil in another location along the first tube 230.

According to one or more embodiments, as a non-limiting example, the inner diameter of the first tube 230 may be designed to be 10-20% larger than the diameter of the untwisted/uncoiled fiber 210. Such coiling may be performed on a twisted fiber 120, 220 or an untwisted/uncoiled fiber 210.

In accordance with one or more methods disclosed herein, as a non-limiting example, if nylon 6,6 is used as the fiber material, the inner diameter of the first tube 230 may be approximately twice the diameter of the untwisted/uncoiled fiber 210.

One of ordinary skill in the art appreciates that the first tubes 130, 230, 330, 430 disclosed herein are not limited to a cylindrical shape and may have various exterior and interior shapes. For example, the shape of the first tube 130, 230, 330, 430 may vary from a cylinder to a different tube-like shape and the fiber can still easily move in the first tube 130, 230, 330, 430 and be constrained from snarling. For example, the inner diameter of the tube may vary along the length. Such a variation may or may not be gradual.

One of ordinary skill in the art will appreciate that the applied rotational force does not need to be provided near to the first tube 130, 230, 330, 430, because the rotational force may travel along the fiber to a soft area at the heated part (or parts) of the first tube 130, 230, 330, 430 in accordance with embodiments disclosed herein.

Embodiments disclosed herein may provide for a continuous production process for artificial muscle fibers. Embodiments may provide a more stable twisting process by providing a mechanical confinement to the twisting process. Further, embodiments disclosed herein may provide for a larger bias angle in the manufactured artificial muscle fiber. For example, a bias angle of 53 degrees has been achieved. Embodiments disclosed herein may provide a bias angle greater than 53 degrees.

While the invention has been described with respect to a limited number of embodiments, those skilled in the art, having benefit of this disclosure, will appreciate that other embodiments can be devised without departing from the scope of the invention as disclosed herein.

What is claimed is:

1. A method of manufacturing an artificial muscle actuator fiber, the method comprising:
   providing a tube having one or more continuous heating sections along a length of the tube; and
   in a continuous process,
   threading an untwisted fiber along the axis of the tube and inside the tube from a first end of the tube towards and passing an opposite second end of the tube;
   providing a tension on the untwisted fiber;
   twisting the untwisted fiber while the fiber is within the tube by applying a rotational force to the untwisted fiber such that the fiber is continuously twisted at a twisting point that is intermediate the first end of the tube and the opposite second end of the tube,
   advancing twists, formed by twisting the previously untwisted fiber, towards the opposite second end of the tube,
   wherein the tube is configured to prevent snarling during the twisting of the untwisted fiber,
   providing an inner diameter of the tube to be 10% to 20% larger than a diameter of the untwisted fiber, and
   wherein the tube is further provided as a heater to raise the localized temperature of a cross-section of the tube to a predetermined temperature.

2. The method of claim 1, wherein the predetermined temperature is selected to be between the glass transition temperature of the fiber and the melting temperature of the fiber.

3. The method of claim 1, wherein the untwisted fiber comprises a polymer fiber selected from the group consisting of Nylon 6, Nylon 6,6, polyethylene, polyvinylidene fluoride, Nylon 6,10, Nylon 6,12, liquid crystalline polymers, polyarylate, and combinations thereof.

4. The method of claim 1, wherein the untwisted fiber comprises carbon nanotubes (CNT).

5. The method of claim 1, further comprising: applying a coating to the twisted or untwisted fiber.

6. The method of claim 1, further comprising: applying a coating to the fiber while the fiber is inside the tube.

7. The method of claim 1, further comprising: removing moisture from the untwisted fiber prior to threading the untwisted fiber along the axis of the tube.

8. The method of claim 1, further comprising: supplying an inert gas inside the tube.

9. The method of claim 1, further comprising: supplying a lubricant inside the tube during the twisting.

10. The method of claim 1, further comprising: threading the twisted fiber along an axis of a second tube, wherein the second tube comprises a second heater to raise the temperature of a cross-sectional area of the second tube to a second predetermined temperature.

11. The method of claim 10, wherein the second predetermined temperature is greater than the predetermined temperature.

12. The method of claim 1, wherein the tube has a plurality of heating sections; and, in a direction from the first end of the tube towards the opposite second end of the tube, a diameter of a heating section of the tube is larger than a diameter of any preceding section of the tube.

13. The method of claim 12, wherein the twisting of the untwisted fiber forms a coiled fiber inside the heating section of the tube that has a larger diameter than a preceding section of the tube.

\* \* \* \* \*